United States Patent [19]

Ferrini

[11] 4,221,806

[45] Sep. 9, 1980

[54] NOVEL BENZOTHIOPYRAN DERIVATIVES

[75] Inventor: Pier G. Ferrini, Binningen, Switzerland

[73] Assignee: Ciba-Geigy Corporation, Ardsley, N.Y.

[21] Appl. No.: 10,456

[22] Filed: Feb. 8, 1979

[30] Foreign Application Priority Data

Feb. 16, 1978 [LU] Luxembourg .......................... 79077

[51] Int. Cl.² .................... A61K 31/38; C07D 335/06
[52] U.S. Cl. .................... 424/275; 424/263; 546/280; 549/28
[58] Field of Search ................ 260/327 TH; 546/280; 424/263; 424/275; 549/28

[56] References Cited

U.S. PATENT DOCUMENTS

| | | | |
|---|---|---|---|
| 3,008,969 | 11/1961 | Pretka | 260/343.2 |
| 3,937,719 | 2/1976 | Sellstedt et al. | 260/345.2 |

FOREIGN PATENT DOCUMENTS 803803  11/1958  United Kingdom ............ 260/327 TH

*Primary Examiner*—John D. Randolph
*Attorney, Agent, or Firm*—John J. Maitner

[57] ABSTRACT

Novel benzothiopyran derivatives of the general formula

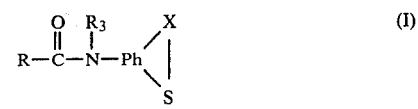

in which R is free, esterified or amidated carboxyl or free or etherified hydroxymethyl, Ph is 1,2-phenylene which contains the group R—CO—NR$_3$— and can be substituted, X is a group of the formula —CO—CR$_1$=CR$_2$—, in which R$_1$ and R$_2$ independently of one another are hydrogen, acyl or a substituted or unsubstituted hydrocarbon radical or a heteroanalogue thereof or together are 3-membered to 5-membered lower alkylene, and R$_2$ can also be free or etherified hydroxyl or hydroxyl esterified by an organic carboxylic acid, and R$_3$ is hydrogen or lower alkyl, possess antiallergic properties and can be used as medicaments.

10 Claims, No Drawings

NOVEL BENZOTHIOPYRAN DERIVATIVES

The invention relates to novel benzothiopyran derivatives of the general formula

in which R is free, esterified or amidated carboxyl, Ph is 1,2-phenylene which contains the group R—CO—NR$_3$— and can be substituted, X is a group of the formula —CO—CR$_1$=CR$_2$—, in which R$_1$ and R$_2$ independently of one another are hydrogen, acyl or a substituted or unsubstituted hydrocarbon radical or a hetero-analogue thereof or together are 3-membered to 5-membered lower alkylene, and R$_2$ can also be free or etherified hydroxyl or hydroxyl esterified by an organic carboxylic acid, and R$_3$ is hydrogen or lower alkyl, in the free form or in the form of a salt, pharmaceutical preparations containing these compounds and the use thereof.

The radical R$_3$ is in particular hydrogen.

Esterified carboxyl is, for example, carboxyl esterified by a substituted or unsubstituted alcohol of aliphatic or aromatic character.

An alcohol of aliphatic character is an alcohol in which the C atom bonded to the hydroxyl group is not a member of an aromatic system, for example an aliphatic alcohol which is unsubstituted or substituted by substituted or unsubstituted aryl or hetero-aryl, for example substituted or unsubstituted phenyl or pyridyl, and is, for example, a lower alkanol, or a cycloaliphatic alcohol, for example a 5-membered to 8-membered cycloalkanol. Examples of carboxyl esterified by a substituted or unsubstituted alcohol of aliphatic character are: lower alkoxycarbonyl, for example methoxy-, ethoxy-, propoxy-, isopropoxy- and butoxy-carbonyl, phenyl-lower alkoxycarbonyl, in particular α- and β-phenyl-lower alkoxycarbonyl, which in the phenyl moiety is unsubstituted or substituted and in which substituted or unsubstituted phenyl and lower alkoxy are, in particular, those mentioned below, for example benzyloxy- and α- and β-phenethoxy-carbonyl, and 5-membered to 8-membered cycloalkoxycarbonyl, for example cyclopentyloxy-, cyclohexyloxy- and cycloheptyloxycarbonyl.

An alcohol of aromatic character is an alcohol in which the C atom bonded to the hydroxyl group is a member of a carbocyclic or heterocyclic aromatic system, for example a phenol substituted or unsubstituted in the phenyl moiety, or a hydroxypyridine substituted by lower alkyl, such as methyl, or lower alkoxy, such as methoxy. Examples of carboxyl esterified by a substituted or unsubstituted alcohol of aromatic character are: phenoxy-, tolyloxy-, anisyloxy- and chlorophenoxy-carbonyl and also 2-, 3- and 4-pyridyloxycarbonyl.

Amidated carboxyl contains, as the amino group, for example a free amino group or an amino group substituted by at least one substituted or unsubstituted hydrocarbon radical of aliphatic character or a hetero-analogue thereof, or one substituted or unsubstituted aryl radical.

In a substituted or unsubstituted hydrocarbon radical of aliphatic character, or a hetero-analogue thereof, the free valency emanates from a non-aromatic C atom. Such a radical is, for example, lower alkyl or lower alkenyl, which can be substituted by substituted or unsubstituted phenyl or naphthyl, or, for example, 5-membered to 8-membered cycloalkyl, such as cyclohexyl, or 4-membered to 7-membered alkylene, which can be lower alkylated, for example methylated, or a monooxa, monoaza or monothia analogue thereof, for example tetra- or pentamethylene or 3-oxa-, 3-aza- or 3-thia-pentamethylene. Examples of carbamyl substituted by at least one such radical are: mono- or di-lower alkylcarbamyl, such as N-methyl- and N,N-diethyl-carbamyl, phenyl-lower alkylcarbamyl which in the phenyl moiety is unsubstituted or substituted as indicated below, such as N-benzyl- or N-(1- or 2-phenethyl)-carbamyl or pyrrolidino-, piperidino-, morpholino-, thiomorpholino- or piperazino-carbonyl or 4-lower alkyl-piperazinocarbonyl, for example 4-methylpiperazinocarbonyl.

A substituted or unsubstituted aryl radical is, for example, substituted or unsubstituted naphthyl or phenyl which is unsubstituted or substituted as indicated below and/or substituted on two adjacent ring atoms by a -OX- group having the meaning defined. Carbamyl groups substituted by such a radical are, for example, N-phenyl-, N-tolyl-, N-anisyl-, N-chlorophenyl- and N-naphthylcarbamyl.

1,2-Phenylene Ph, which contains the group R—CO—NR$_3$—, can also contain, in addition to this group, at least, for example one or two, further substituents, examples of which are lower alkyl, such as those indicated below, for example methyl, lower alkoxy, such as those given below, for example methoxy, halogens, such as those indicated below, for example chlorine, and trifluoromethyl.

Acyl is, for example, acyl derived from an organic carboxylic acid or from free or partially esterified or amidated carbonic acid.

Acyl derived from a carboxylic acid is, for example, lower alkanoyl or substituted or unsubstituted benzoyl, for example acetyl, propionyl, butyryl or benzoyl.

Acyl derived from free or partially esterified or amidated carbonic acid is, for example, free or esterified or amidated carboxyl, such as free carboxyl or carboxyl esterified or amidated as indicated above, for example carboxyl, methoxy- or ethoxy-carbonyl or carbamyl.

Free or etherified hydroxyl is, for example, free hydroxyl or hydroxyl etherified by a lower alkanol or a substituted or unsubstituted phenol, i.e., hydroxyl, lower alkoxy or substituted or unsubstituted phenoxy, for example hydroxyl, methoxy, ethoxy or phenoxy.

Free hydroxyl or hydroxyl esterified by a carboxylic acid is, for example, free hydroxyl or hydroxyl esterified by a lower alkanecarboxylic acid or a substituted or unsubstituted benzoic acid, i.e., hydroxyl, lower alkanoyloxy or substituted or unsubstituted benzoyloxy, especially acetoxy, propionyloxy or benzoyloxy.

A substituted or unsubstituted hydrocarbon radical, or a hetero-analogue thereof, is, for example, a substituted or unsubstituted hydrocarbon radical of aliphatic character or a substituted or unsubstituted aromatic hydrocarbon radical, or a hetero-analogue thereof.

3-membered to 5-membered lower alkylene can be straight-chain or branched and is, for example, 1,3-propylene, 1,4-butylene, 1,5-pentylene or 2- or 3-methyl-1,4-butylene.

In a substituted or unsubstituted hydrocarbon radical of aliphatic character the free valency emanates from a non-aromatic C atom. Such a radical is, for example, an aliphatic hydrocarbon radical which is unsubstituted or substituted by substituted or unsubstituted phenyl, for example a lower alkyl radical or a cycloaliphatic hydrocarbon radical, such as adamantyl or monocyclic 5-membered to 8-membered cycloalkyl or cycloalkenyl, for example 1-cycloalkenyl. Examples of such radicals are, in particular: methyl, ethyl, isopropyl and butyls, benzyl and methyl-, methoxy- and chloro-benzyls, cyclopentyl, cyclohexyl, 1-cyclohexenyl, cycloheptyl and 1-cycloheptenyl.

A substituted or unsubstituted aromatic hydrocarbon radical, or a hetero-analogue thereof, has, for example, 5 or 6 ring members and up to 2 hetero-atoms, such as nitrogen, oxygen or sulfur atoms, and is, for example, substituted or unsubstituted phenyl, such as one of those mentioned below, or a 5-membered or 6-membered hetero-aryl radical containing a nitrogen, oxygen or sulfur atom, for example one of those indicated below. Examples are, in particular, phenyl or pyridyl which are unsubstituted or substituted by methyl, methoxy or chlorine.

In this specification:

Substituted or unsubstituted phenyl and naphthyl, and also phenyl in substituted or unsubstituted benzoyl, benzoyloxy and aromatic alcohols, is, for example, unsubstituted or mono- or poly-substituted, for example mono- or di-substituted, phenyl or naphthyl, substituents being, in particular, lower alkyl, lower alkoxy or halogens, for example those indicated below, hydroxyl and also trifluoromethyl, such as phenyl, naphthyl, o-, m- or p-tolyl, o-, m- or p-anisyl, o-, m- or p-chlorophenyl or 2,4-, 3,5- or 2,6-dichlorophenyl.

Substituted or unsubstituted hetero-aryl and hetero-aryl in hetero-aromatic alcohols preferably has 5 or 6 ring members and contains up to two nitrogen, oxygen and/or sulfur atoms as the hetero-atom or -atoms and is for example, unsubstituted or mono- or poly-substituted pyridyl, thienyl or furyl, substituents being lower alkyl, lower alkoxy and halogens, in particular, in each case, those indicated above, such as 2-, 3- or 4-pyridyl, 6-methyl-2-pyridyl, 6-methoxy-2-pyridyl or 2- or 3-thienyl.

Lower alkyl contains, for example, not more than 7 and in particular not more than 4 C atoms and can be straight-chain or branched and bonded in any position, such as methyl, ethyl, propyl or n-butyl or also isopropyl or sec.- or iso-butyl.

Lower alkoxy and also lower alkoxy in lower alkoxycarbonyl has, for example, not more than 7 and in particular not more than 4 C atoms and can be straight-chain or branched and bonded in any position, such as methoxy, ethoxy, propoxy, isopropoxy, butoxy or amyloxy.

Lower alkanoyl and also lower alkanoyl in lower alkanoyloxy contains, for example, not more than 7 and in particular not more than 4 C atoms and can be straight-chain or branched, such as acetyl, propionyl, butyryl or isobutyryl.

Halogen is, for example, halogen with an atomic number of not more than 35, such as fluorine, chlorine or bromine.

Salts of compounds of the general formula (I), in which R, $R_1$ and/or $R_2$ is carboxyl, are salts with bases, in particular corresponding pharmaceutically acceptable salts, such as alkali metal salts or alkaline earth metal salts, for example sodium, potassium, magnesium or calcium salts, and also ammonium salts with ammonia or amines, such as lower alkylamines or hydroxylower alkylamines, for example trimethylamine, triethylamine or di- or tri-(2-hydroxyethyl)-amine.

The novel compounds have valuable pharmacological properties. In particular they have an antiallergic action, which can be demonstrated, for example, in rats in doses as low as 1 mg/kg on oral administration in the passive cutaneous anaphylaxis test (PCA reaction), which is carried out analogously to the method described by Goose and Blair, Immunology, Volume 16, page 749 (1969), the passive cutaneous anaphylaxis being produced by the procedure described by Ovary, Progr. Allergy, Volume 5, page 459 (1958). They also effect inhibition of the immunologically induced release of histamine, for example from peritoneal cells of Nippostrongylus brasiliensis-infested rats in vitro, Dukor et al., 11th Symposium of the Collegium internationale allergologicum, Heidelberg, May 1976, and they are also highly active in diverse bronchoconstriction models, as can be shown, for example, in a dosage as low as about 1 to about 3 mg/kg, administered intravenously, with the aid of the bronchoconstriction induced by IgE antibodies in rats, and in the dosage range of from about 1 mg/kg, administered intravenously, with the aid of the bronchoconstriction induced by IgG antibodies in guineapigs. The compounds of the present invention are, accordingly, useful as inhibitors of allergic reactions, for example in the treatment and prophylaxis of allergic diseases, such as asthma, including both extrinsic and intrinsic asthma, or other allergic diseases, such as hayfever, conjunctivitis, urticaria and eczema.

The invention relates in particular to compounds of the general formula I in which R is carboxyl, carboxyl esterified by an alcohol of aliphatic or aromatic character, or free carbamyl or carbamyl which is substituted by at least one substituted or unsubstituted hydrocarbon radical of aliphatic character, or a hetero-analogue thereof, or substituted or unsubstituted aryl radical, Ph is 1,2-phenylene which contains the group R—CO—NR$_3$— and is substituted or unsubstituted, X is a group —CO—CR$_1$=CR$_2$—, in which R$_1$ and R$_2$ independently of one another are hydrogen, lower alkanoyl, benzoyl, free carboxyl or carboxyl esterified or amidated as indicated above for R, or a substituted or unsubstituted hydrocarbon radical of aliphatic character or aromatic hydrocarbon radical or a hetero-analogue of the latter, or together are 1,3-, 1,4- or 1,5-lower alkylene, and R$_2$ can also be free hydroxyl or hydroxyl etherified by a lower alkanol or esterified by a lower alkanecarboxylic acid, and R$_3$ is hydrogen or lower alkyl, the substituents or aromatic and hetero-aromatic groups being, in each case, in particular lower alkyl, such as methyl, lower alkoxy, such as methoxy, halogen, such as chlorine, hydroxyl and trifluoromethyl, in the free form or in the form of a salt.

The invention relates in particular to compounds of the general formula I in which R is carboxyl, carboxyl esterified by a lower alkanol, which is unsubstituted or substituted by substituted or unsubstituted phenyl, or a substituted or unsubstituted phenol, or free carbamyl or carbamyl which is monosubstituted by lower alkyl, substituted or unsubstituted phenyl-lower alkyl or substituted or unsubstituted phenyl, or disubstituted by lower alkyl or lower alkylene, or a hetero-analogue of the latter, Ph is 1,2-phenylene which contains the group R—CO—NR$_3$— and is substituted or unsubstituted, X is a group —CO—CR$_1$=CR$_2$—, in which R$_1$ and R$_2$ independently of one another are hydrogen, lower alkanoyl, such as acetyl, free carboxyl or carboxyl esterified by a lower alkanol, such as methanol, lower alkyl which is unsubstituted or substituted by phenyl, which in turn can be substituted, or substituted or unsubstituted phenyl or 5-membered to 6-membered hetero-aryl containing a nitrogen, oxygen or sulfur atom, or together are tri-, tetra- or pentamethylene, and $R_2$ can also be free hydroxyl or hydroxyl etherified by a lower alkanol, such as methanol, or esterified by a lower alkanecarboxylic acid, such as acetic acid, and $R_3$ is hydrogen or lower alkyl, substituents of phenyl, phenol, 1,2-phenylene Ph and hetero-aryl being lower alkyl, such as methyl, lower alkoxy, such as methoxy, halogen, such as chlorine, hydroxyl and trifluoromethyl, in the free form or in the form of a salt.

The invention relates especially on the one hand to compounds of the general formula Ia

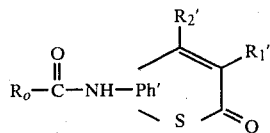

and on the other hand to compounds of the general formula Ib

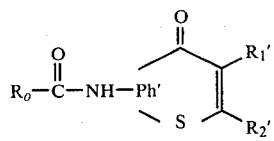

in which, in each case, $R_0$ is carboxyl, lower alkoxycarbonyl, such as methoxy- or ethoxy-carbonyl, phenyl-lower alkoxycarbonyl which in the phenyl moiety is unsubstituted or substituted as indicated below, such as benzyloxycarbonyl, or free carbamyl or carbamyl which is monosubstituted or disubstituted by lower alkyl, such as methyl or ethyl, or disubstituted by tetra- or pentamethylene or 3-oxa-, 3-aza- or 3-thia-pentamethylene, Ph' is 1,2-phenylene which contains the group $R_0$—CO—NH— and additionally is unsubstituted or substituted as indicated below, and $R_1'$ and $R_2'$ together are tri-, tetra- or pentamethylene, or $R_1'$ is hydrogen, lower alkanoyl, such as acetyl, carboxyl, lower alkoxycarbonyl, such as methoxy- or ethoxy-carbonyl, lower alkyl, such as methyl, or phenyl or pyridyl which are unsubstituted or substituted as indicated below and $R_2'$ has one of the meanings defined for $R_1'$ or is hydroxyl, lower alkoxy, such as methoxy, or lower alkanoyloxy, such as acetoxy, substituents of substituted phenyl-lower alkoxycarbonyl R', additionally substituted 1,2-phenylene Ph' and of substituted phenyl and pyridyl $R_1'$ and/or $R_2'$ being lower alkyl, such as methyl, lower alkoxy, such as methoxy, halogen, such as chlorine, hydroxyl and trifluoromethyl, in each case in the free form or in the form of a salt.

The invention relates very particularly to compounds of the general formula Ia in which $R_0$ is carboxyl or lower alkoxycarbonyl having not more than 5 C atoms, such as methoxy- or ethoxy-carbonyl, Ph' is 1,2-phenylene which contains the group $R_0$—CO—NH, for example bonded in the 4- or 5-position, and in one of the free positions can be substituted by lower alkyl or lower alkoxy, each having not more than 4 C atoms, such as methyl or methoxy, or hydroxyl or halogen, such as chlorine, and $R_1'$ and $R_2'$ independently of one another are hydrogen, lower alkyl having not more than 4 C atoms, such as methyl, or phenyl, in each case in the free form or in the form of a salt.

The invention relates very particularly to compounds of the formula

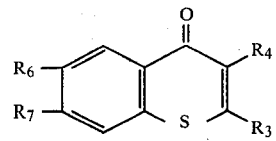

in which one of the radicals $R_6$ and $R_7$ is a group of the formula $R_0'$—CO—NH, in which $R_0'$ is carboxyl or, less importantly, lower alkoxycarbonyl having not more than 5 C atoms, such as methoxy- or ethoxy-carbonyl, and the other is hydrogen, and $R_3$ and $R_4$ independently of one another are hydrogen or lower alkyl having not more than 4 C atoms, such as methyl, in the free form or in the form of a salt.

The novel compounds can be prepared by processes known per se.

A preferred procedure comprises, for example, reacting a compound of the general formula II

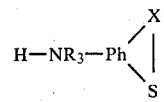

in which Ph, $R_3$ and X are as defined, or a salt thereof, with one equivalent of an oxalic acid, which can be functionally modified, or a salt thereof, and, if desired, converting a compound thus obtained into another compound of the general formula (I) and/or converting a resulting salt-forming compound into a salt or a resulting salt into the free compound.

Salts of compounds of the formula II are, for example, hydrohalides, such as hydrochlorides, thereof, and also salts with oxalic acid or a monoester or monoamide thereof.

Functional derivatives of oxalic acid are monofunctional or preferably difunctional derivatives of oxalic acid, for example those of the formula R-Y, in which Y is a free, esterified or amidated carboxyl group or a carboxyl group converted to an anhydride, for example with a hydrogen halide acid, or a group of the formula —C(=O)—N$_3$ or —C(=O)—N$_2^{\oplus}$A$^{\ominus}$, in which A$^{\ominus}$ is the anion of a mineral acid, for example chloride, bromide or tetrafluoborate. Examples are, in particular: symmetrical oxalic acid diesters, such as di-lower alkyl esters, and diamides of the formula R-R and also free, esterified or amidated halogeno-oxalic acids of the formula R-Co-Hal, in which Hal is chlorine or bromine.

The reaction can be carried out in a conventional manner, especially in the manner known from the literature for analogous reactions, if necessary in the presence of a condensing agent, for example, in the case of the reaction with an ester-halide or amide-halide of oxalic acid, in the presence of a basic condensing agent, such as a tertiary organic nitrogen base, for example triethylamine or pyridine, or of an alkali metal hydroxide or alkali metal carbonate, for example sodium hydroxide or potassium hydroxide, or, for example, in the case of the reaction with oxalic acid, in the presence of a condensing agent which effects dehydration of the ammonium salt first formed, such as in the presence of a water-binding agent, for example of dicyclohexylcarbodiimide or of an isonitrile, such as tert.-butylisonitrile, or of a mineral acid, for example hydrochloric acid, or of an acid anhydride, for example phosphorus pentoxide, and/or in an inert solvent, preferably an inert polar solvent, such as a N,N-dialkylamide, for example in N,N-dimethylformamide or N,N-dimethylacetamide.

The novel compounds can also be prepared by converting R′ in a compound of the formula

(III)

in which R′ is a radical which can be converted to the desired group of the formula RCO—NR₃—, into the group of the formula RCO—NR₃— and, if desired, converting a compound thus obtainable into another compound of the formula I and/or converting a resulting salt into the free compound or into another salt or converting a resulting salt-forming compound into a salt.

A radical which can be converted to the group of the formula RCO—NR₃— is, for example, a radical which can be converted to the said group by solvolysis, i.e., hydrolysis, alcoholysis (reaction with the alcohol corresponding to the desired esterified carboxyl group R—) and/or aminolysis (reaction with ammonia or an amine corresponding to the desired amidated carboxyl group), preferably a group of the formula $X_1$—NR₃—, in which $X_1$ is a functionally modified oxalo group which differs from a free, esterified or amidated oxalo group and can be converted into the latter. Such functionally modified oxalo groups are preferably those which contain, as a functionally modified α-carbonyl grouping, thioxomethylene, iminomethylene or an esterified and/or etherified dihydroxymethylene grouping and/or contain, as a functionally modified carboxyl group, a functionally modified carboxyl group which differs from an esterified or amidated carboxyl group. Esterified and/or etherified dihydroxymethylene groupings are, for example, dihydroxymethylene groups esterified with a hydrogen halide acid, such as hydrochloric acid, and/or etherified with a lower alkanol, such as methanol or ethanol. Examples are, in particular, dihalogenomethylene groupings, such as dichloromethylene, lower alkoxyhalogenomethylene groupings, such as methoxy- or ethoxy-chloromethylene, or di-lower alkoxymethylene groupings, such as dimethoxy- or diethoxymethylene. Functionally modified carboxyl groupings which differ from esterified or amidated carboxyl groups are, for example, the cyano group, carboxyl groups converted to an anhydride, such as halogenocarbonyl, for example chlorocarbonyl, imino-ester groupings, such as imide- or amide-halide groupings, for example iminochloromethyl or aminodichloromethyl, iminoether groupings, such as lower alkyl- or lower alkyleneimino-ether groupings, for example methoxy- or ethoxy-iminomethylene, 4,4- or 5,5-dimethyloxazolin-2-yl or 4,4,6-trimethyl-dihydro-oxazin-2-yl, amidino groups, such as amidino or lower alkylamidino, for example methylamidino, ortho-acid groupings esterified with a hydrogen halide acid, such as hydrochloric acid, and/or etherified with a lower alkanol, such as tri-lower alkoxy-, lower alkoxyhalogeno- or trihalogeno-methyl groups, in particular trimethoxymethyl or triethoxymethyl, ethoxydichloromethyl or trichloromethyl, or free or esterified thiocarboxyl groups, such as lower alkylthiocarbonyl groups, for example ethylthiocarbonyl. Such groups $X_1$ can, for example, be converted into the oxalo group by hydrolysis. Groups $X_1$ which contain, as a functionally modified carboxyl group, an imino-ether, ortho-ester or ester-halide grouping and/or contain, as a functionally modified α-carbonyl group, thioxomethylene or iminomethylene or an esterified or etherified dihydroxymethylene group can also be hydrolysed to esterified oxalo groups. Likewise, groups $X_1$ which contain, as a functionally modified carboxyl group, the cyano group or an amidino or imide- or amide-halide grouping and/or contain, as a functionally modified α-carbonyl group, thioxomethylene or iminomethylene or an etherified or esterified dihydroxymethylene group can be hydrolysed to amidated carboxyl groups. The hydrolysis can be carried out in a conventional manner, if necessary in the presence of a basic or preferably acid hydrolysing agent, such as of an alkali metal hydroxide, such as sodium hydroxide or potassium hydroxide, or preferably of a protonic acid, preferably a mineral acid, for example a hydrogen halide acid, such as hydrochloric acid, or of an organic carboxylic or sulfonic acid, for example acetic acid or p-toluenesulfonic acid.

Thus, for example, any functionally modified oxalo group $X_1$ which differs from an esterified or amidated oxaloamino group RCO— can be converted to the free oxalo group by hydrolysis, for example in the presence of an acid or basic agent, such as of a mineral acid, for example hydrochloric acid, or of an alkali metal hydroxide, for example sodium hydroxide solution or potassium hydroxide solution, and in the case of the hydrolysis of cyanocarbonyl groups or of thio-oxalo groups to the oxalo group preferably under acid conditions and/or in the presence of an oxidising agent, for example hydrogen peroxide.

If necessary, the reaction is carried out in a polar solvent, such as a lower alkanol, ketone or ether, for example in ethanol, acetone or dioxan, and/or with cooling or warming, for example at about 0° C. to about 100° C.

Functionally modified oxalo groups which contain, as a functionally modified carboxyl group, a carboxyl group which has been converted to an anhydride, such as halogenocarbonyl, for example chlorocarbonyl, cyanocarbonyl or a lower alkyleneimino-ether grouping, for example 4,4- or 5,5-dimethyl-oxazolin-2-yl or 4,4,6-trimethyl-dihydro-oxazin-2-yl, can also be converted to esterified oxalo groups by conventional alcoholysis, i.e. reaction with the corresponding alcohol. In the case of the alcoholysis of carboxyl groups which have been converted to an anhydride, the reaction is advantageously carried out in the presence of a basic condensing agent, for example of pyridine or triethylamine, whilst the alcoholysis of a lower alkyleneimino-ether grouping is preferably carried out under acid conditions, for example in the presence of hydrochloric acid, p-toluenesulfonic acid or acetic acid. Analogously, a functionally modified oxalo group which contains a carboxyl group which has been converted to an anhydride can also be converted to an amidated oxalo group R—C(=O)— by ammonolysis or aminolysis, i.e. reaction with ammonia or a corresponding primary or secondary amine, preferably in the presence of a basic condensing agent, for example of sodium hydroxide, pyridine or triethylamine.

Further radicals R' which can be converted to groups of the formula RCO—$NR_3$— are, for example, groups which can be converted to the said groups by oxidation, especially those of the formula $X_2$—$NR_3$—, in which $X_2$ is a glyoxyl group, which can be in the form of a hydrate and can be converted by oxidation to the oxalo group of the formula R—C(=O)—, in which R is carboxyl. This group can advantageously be formed in situ in the course of the oxidation reaction, for example from the acyl group of an aliphatic or araliphatic carboxylic acid which can be $\alpha,\beta$-unsaturated or $\alpha,\beta$-dihydroxylated, a glycoloyl group, which can be esterified on the hydroxyl group, or a glycyl group, or set free from one of its functional derivatives, for example one of its acetals or imines. Acyl groups of carboxylic acids which can be $\alpha,\beta$-unsaturated or $\alpha,\beta$-dihydroxylated are, for example, alkanoyl groups, such as lower alkanoyl, for example acetyl, acyl groups of $\alpha,\beta$-unsaturated aliphatic mono- or di-carboxylic acids, for example acryloyl, crotonyl or the acyl group of free or functionally modified fumaric or maleic acid, acyl groups of $\alpha,\beta$-unsaturated araliphatic carboxylic acids, for example substituted or unsubstituted cinnamoyl, or acyl groups of aliphatic $\alpha,\beta$-dihydroxydicarboxylic acids, such as of tartaric acid, or monofunctional carboxy derivatives, such as esters or amides, thereof. Esterified glycoloyl groups are, for example, glycoloyl groups esterified on the hydroxyl group with a mineral acid, such as a hydrogen halide acid, for example with hydrochloric acid or hydrobromic acid, or with a carboxylic acid, for example with acetic acid or substituted or unsubstituted benzoic acid. Acetalised glyoxyloyl groups are, for example, glyoxyloyl groups acetalised with lower alkanols or a lower alkanediol, such as dimethoxy-, diethoxy- or ethylenedioxyacetyl. Imines of glyoxyloyl groups are, for example, substituted or unsubstituted N-benzylimines or N-(2-benzthiazolyl)-imines thereof or imines with 3,4-di-tert.-butyl-o-quinone. Further radicals which can be converted to the oxalo group by oxidation are, for example, substituted or unsubstituted 2-furoyl groups, such as 2-furoyl groups which contain an acetalised formyl group, such as diethoxymethyl, in the 5-position. Groups which can be oxidised to esterified oxaloamino groups of the formula R—C(=O)—, in which R is esterified carboxyl, are etherified glycoloyl groups, such as lower alkoxyacetyl. Radicals which can be oxidised to free, esterified or amidated oxaloamino groups are also formylmethylamino groups, which can be in the form of a hydrate or can be acetalised, or free or functionally modified carboxymethylamino groups or carboxymethyleneimino groups, for example of the formula OH-C—$CH_2$—$NR_3$, R—$CH_2$—$NR_3$— or R—CH=N—.

The oxidation can be carried out in a conventional manner by reaction with a suitable oxidising agent. Suitable oxidising agents are, in particular, oxidising heavy metal compounds, such as silver compounds, for example silver nitrate or silver picolinate, oxyacids of heavy metals, for example of manganese-IV, manganese-VII, chromium-VI and iron-VI, or of halogens, or their anhydrides or salts, such as chromic acid, chromium dioxide, potassium dichromate, potassium permanganate, manganese dioxide, potassium ferrate, sodium chlorite in the presence of sulfamic acid, sodium hypochlorite in the presence of nickel chloride or sodium iodate, sodium periodate or lead tetraacetate. The reaction with these oxidising agents is carried out in a conventional manner, for example in an inert solvent, such as acetone, acetic acid, pyridine or water, or a, preferably aqueous, inert solvent mixture, at normal temperature or if necessary with cooling or warming, for example at about 0° C. to about 100° C. The oxidation of free or etherified glycoloyl groups to free or esterified oxalo groups is, for example, advantageously carried out with potassium permanganate in aqueous pyridine or acetone at room temperature. Acetalised glyoxyloyl groups and iminoacetyl groups are preferably oxidised under acid conditions, for example with potassium dichromate in sulfuric acid, and acyl groups of $\alpha,\beta$-dihydroxylated aliphatic carboxylic acids, such as the acyl radical of tartaric acid, are advantageously oxidised with periodic acid, whilst for the oxidation of a glycyl group preferably potassium ferrate in an alkaline medium, for example at pH=10-13, for example 11.5, or organic silver salts, such as silver picolinate, are used. Groups of the formula R—CH=N— are preferably oxidised with an organic per-acid, for example with peracetic acid or m-chloroperbenzoic acid, in an inert solvent, for example methylene chloride, chloroform or benzene.

Another procedure comprises subjecting a compound of the general formula

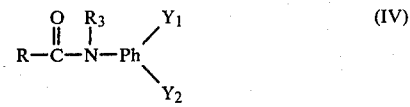

(IV)

in which either $Y_1$ is a group —$CR_2$=$CR_1$—$Y_3$ or —CO—$CR_1$=$CR_2$—$Y_4$ and $Y_2$ is free or etherified mercapto or mercapto esterified with a carboxylic acid, or $Y_1$ is hydrogen and $Y_2$ is a group —S—$CR_2$=$CR_1$—$Y_3$ or —S—CO—$CR_1$=$CR_2$—$Y_4$, or $Y_1$ is a group —C(C)$Y_5$ and $Y_2$ is a group —S—C(O)—$Y_6$, and in which $Y_3$ is free or functionally modified carboxyl and $Y_4$ is free, etherified or esterified mercapto, and a group —CO—$CR_1$=$CR_2$—OH or —S—CO—$CR_1$=$CR_2$—OH can also be in the tautomeric oxo form represented by the formula —CO—$CHR_1$—C(O)—$R_2$ or —S—CO—$CHR_1$—C(O)—$R_2$ respectively, and one of the radicals $Y_5$ and $Y_6$ is a —$CH_2R_1$ group and the other is a $R_2$ group or etherified mercapto, and R, Ph, $R_1$, $R_2$ and $R_3$ are as defined, or a salt thereof to intramolecular cyclisation and, in a compound, which may be obtained, of the formula

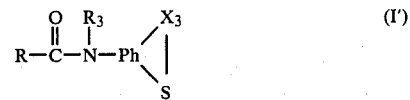

(I')

in which $X_3$ is a group —C(=$Y_0$)—$CR_1$=$CR_2$— and $Y_0$ is a functionally modified oxo group, converting $Y_0$ into the oxo group, if necessary separating a resulting mixture of isomers into the components and, if desired, carrying out one or more of the said optional additional operations.

Functionally modified carboxyl is, for example, cyano or esterified carboxyl or carboxyl which has been converted to an anhydride. Esterified carboxyl is preferably carboxyl esterified with a lower alkanol, for example methoxycarbonyl or ethoxycarbonyl. Carboxyl which has been converted to an anhydride is, for example, carboxyl converted to an anhydride with a carboxylic acid, such as with a lower alkanecarboxylic acid or a substituted or unsubstituted benzoic acid, or with a hydrogen halide acid, for example acetoxycarbonyl, benzoyloxycarbonyl or bromo- or chloro-carbonyl.

A functionally modified oxo group $Y_0$ is, for example, a thioxo group or in particular an imino group, preferably the primary imino group, which can also be in the form of an acid addition salt, for example of the hydrochloride.

Etherified mercapto is, for example, lower alkylthio, for example methylthio or ethylthio.

Esterified mercapto is, for example, mercapto esterified with a carboxylic acid.

Mercapto esterified with a carboxylic acid is, for example, lower alkanoylthio or substituted or unsubstituted benzoylthio, for example acetylthio or benzoylthio.

Salts of compounds of the general formula (IV) are in particular metal salts, such as alkali metal salts, for example sodium or potassium salts, of compounds containing a phenolic mercapto group $Y_2$, carboxyl group $Y_3$ and/or R, enolic hydroxyl group $Y_4$ and/or $R_1CH_2$ groups $Y_5$ or $Y_6$.

The intramolecular cyclisation can be carried out in a conventional manner, especially in the manner known from the literature for analogous reactions, if necessary in the presence of a condensing agent and/or at elevated temperature, for example the boiling point of the reaction mixture.

Condensing agents for this reaction are, for example, the customary acid or basic condensing agents. Acid condensing agents are, for example, protonic acids, such as carboxylic acids, for example acetic acid or trifluoroacetic acid, organic sulfonic acids, for example benzene-, p-toluene-, p-bromobenzene- or methane-sulfonic acid, or, in particular, mineral acids and if appropriate their acid salts, such as hydrochloric acid, hydrobromic acid or hydriodic acid, sulfuric acid, potassium bisulfate, phosphoric acid or polyphosphoric acid, or acid anhydrides, for example acetic anhydride, acetyl chloride, phosphorus pentoxide or phosphorus oxychloride, or Lewis acids, preferably halides, for example fluorides, chlorides or bromides, of elements of principal group 3, 4 or 5 or of sub-group 2 of the periodic table, such as of boron, aluminium, antimony, zinc, tin or cadmium, for example aluminium trichloride or aluminium tribromide, boron trifluoride, zinc chloride or antimony pentachloride. Basic condensing agents are, for example, weakly or moderately basic condensing agents, such as alkali metal salts or ammonium salts of carboxylic acids, for example sodium acetate, or tertiary organic nitrogen bases, for example pyridine or triethylamine, or strongly basic condensing agents, such as alkali metals or their hydrides, amides, alcoholates or hydrocarbon compounds, for example sodium, potassium, sodium hydride, sodium amide, diisopropylamine-lithium, sodium methylate, sodium ethylate or trityl-sodium.

Inert solvents are, for example, polar inert solvents, such as an excess of the acids, acid anhydrides or tertiary nitrogen bases cited as condensing agents, alcohols, for example methanol or ethanol, glycol, glycol monomethyl ether or diethylene glycol monomethyl ether, ketones, for example acetone, N,N-dialkylcarboxylic acid amides, for example dimethylformamide, sulfoxides, for example dimethylsulfoxide, or carboxylic acids, such as lower alkanoic acids, or their anhydrides, for example acetic acid, acetic anhydride or acetyl chloride.

The conversion of an intermediate of the formula I', which may be obtained, is effected, for example, by mild hydrolysis and can take place at the same time as or after the cyclisation and in the latter case is effected, for example, by the brief action of an aqueous acid solution, for example of hydrochloric acid.

Thus, in a preferred embodiment of the above process, for example, a compound of the general formula IV in which $Y_1$ is a group of the formula $-CR_2=C-R_1-Y_3$, $Y_2$ is hydrogen or a substituted or unsubstituted hydrocarbon radical, or a hetero-analogue thereof, $R_2$ is free or etherified mercapto or mercapto esterified with a carboxylic acid and $Y_3$ is free or esterified carboxyl or carboxyl which has been converted to an anhydride, or cyano, can be converted, if necessary in the presence of an acid condensing agent, to compounds of the general formula I in which $-SX-$ is a group $-SO-C-CR_1=CR_2-$. When the starting materials used are those in which $Y_3$ is free or esterified carboxyl, the condensing agent used is, for example, a phosphoric acid anhydride, such as phosphorus pentoxide or phosphorus pentachloride, or a protonic acid, for example hydriodic acid, hydrochloric acid or hydrobromic acid, sulfuric acid or trifluoroacetic acid. When using a starting material in which $Y_2$ is etherified mercapto and $Y_3$ is cyano, the cyclisation is preferably carried out in the presence of a Lewis acid, for example of aluminium trichloride, and in this case the intermediate of the formula I', which is first formed, is hydrolysed in the acid medium used for working up.

In another preferred embodiment of the above process, for example, a compound of the general formula IV in which $Y_1$ is a group of the formula $-COCH-R_1-CO-R_2$ and $Y_2$ is free or etherified mercapto, or $Y_1$ is a group of the formula $-SCR_2=CR_1-Y_3$ and $Y_2$ is hydrogen, and in which $R_2$ is hydrogen or a substituted or unsubstituted hydrocarbon radical, or a hetero-analogue thereof, and $Y_3$ is free or esterified carboxyl or carboxyl which has been converted to an anhydride with a hydrogen halide acid, for example with hydrochloric acid, can be cyclised in the presence of an acid condensing agent to a compound of the general formula I in which $-XS-$ is a group $-COCR_1-CR_2S-$. The acid condensing agent used is preferably a mineral acid, for example sulfuric acid or polyphosphoric acid, hydriodic acid or hydrobromic acid in acetic acid, or an acid anhydride, for example phosphorus pentoxide or phosphorus pentachloride, when the starting materials used are those in which $Y_1$ is a group $-S-CR_2=CR_1-Y_3$ and $Y_3$ is free or esterified carboxyl, or preferably a Lewis acid, for example aluminium trichloride, when the starting materials used are those in which $Y_1$ is a group $-S-CR_2-CR_1-Y_3$ and $Y_3$ is halogenocarbonyl, such as chlorocarbonyl.

In a further preferred embodiment of the above process, for example, a compound of the general formula IV in which $Y_1$ is free or esterified carboxyl and $Y_2$ is a group $-S-CO-CH_2R_1$, and $R_2$ is hydrogen or a substituted or unsubstituted hydrocarbon radical, or a hetero-analogue thereof, can be cyclised to compounds of the general formula I in which $-SX-$ is a group $-S-COCR_1=C(OH)-$. The reaction is preferably carried out in the presence of a basic condensing agent, in particular of a strongly basic condensing agent, for example sodium, sodium hydride or sodium ethylate.

A compound of the general formula I which is obtainable according to the invention can be converted to another compound of the general formula I in a manner known per se.

Thus, for example, a free carboxyl group R can be converted in a conventional manner, for example by treatment with a diazo-lower alkane which is unsubstituted or substituted by substituted or unsubstituted aryl or hetero-aryl, or a tri-lower alkyloxonium or tri-lower alkylcarboxonium, such as hexachloroantimonate or hexafluorophosphate, or, in particular, by reaction with the corresponding alcohol or a reactive derivative, such as a N,N-di-lower alkyl alkanoic acid amide acetal, for example a N,N-dimethyl formamide di-lower alkyl acetal, a salt of a N,N,O-tri-lower alkyl formamide, for example a N,N,O-tri-lower alkyl formamidemethosulphate, or a carboxylic, phosphorous, sulfurous or carbonic acid ester, for example a lower alkanecarboxylic acid ester, tri-lower alkyl phosphite or di-lower alkyl sulfite, in the presence of a weakly to moderately basic condensing agent, into esterified carboxyl.

The reaction with the corresponding alcohol itself can advantageously be carried out in the presence of an acid catalyst, such as a protonic acid, for example hydrochloric acid or hydrobromic acid, sulfuric acid, phosphoric acid, boric acid, benzenesulfonic acid and/or toluenesulfonic acid, in an inert solvent, especially an excess of the alcohol employed, and if necessary in the presence of a water-binding agent and/or with removal of the water of reaction by distillation, for example azeotropically, and/or at elevated temperature.

The reaction with a reactive derivative of the corresponding alcohol can be carried out in a conventional manner, for example, when the starting material is a carboxylic, phosphorous, sulfurous or carbonic acid ester, in the presence of an acid catalyst, such as one of those mentioned above, in an inert solvent, such as an aromatic hydrocarbon, for example in benzene or toluene, or an excess of the alcohol derivative employed or of the corresponding alcohol, the water of reaction being distilled off if necessary, for example as an azeotrope. When the starting material is a mineral acid ester or sulfonic acid ester, the acid to be esterified is advantageously employed in the form of a salt, for example the sodium or potassium salt, and if necessary the reaction is carried out in the presence of a basic condensing agent, such as of an inorganic base, for example sodium hydroxide or carbonate, potassium hydroxide or carbonate or calcium hydroxide or carbonate, or of a tertiary organic nitrogen base, for example triethylamine or pyridine, and/or in an inert solvent, such as one of the above tertiary nitrogen bases or a polar solvent, for example in dimethylformamide, and/or at elevated temperature.

The reaction with an olefin can be carried out, for example, in the presence of an acid catalyst, for example a Lewis acid, for example boron trifluoride, or a sulfonic acid, for example p-toluenesulfonic acid, or, in particular, in the presence of a basic catalyst, for example of sodium hydroxide or potassium hydroxide, advantageously in an inert solvent, such as an ether, for example in diethyl ether or tetrahydrofuran.

A free carboxyl group R can also be converted to an amidated carboxyl group R by reaction with ammonia or an amine which contains at least one hydrogen atom, in a conventional manner, with dehydration of the ammonium salt formed as an intermediate, for example by azeotropic distillation with benzene or toluene or dry heating.

The conversions, described above, of free carboxyl groups R to esterified or amidated carboxyl groups R can, however, also be carried out by first converting a compound of the formula I, in which R is carboxyl, into a reactive derivative in a conventional manner, for example by means of a halide of phosphorus or sulfur, for example by means of phosphorus trichloride or phosphorus tribromide, phosphorus pentachloride or thionyl chloride, to an acid halide or, by reaction with a corresponding alcohol or amine to a reactive ester, i.e. esters with electron-attracting structures, such as the ester with phenol, thiophenol, p-nitrophenol or cyanomethyl alcohol, or a reactive amide, for example the amide derived from imidazole or 3,5-dimethylpyrazole, and then reacting the resulting reactive derivative in a conventional manner, for example as indicated below for trans-esterification, trans-amidation or mutual conversion of esterified and amidated carboxyl groups R, with a corresponding alcohol, ammonia or the corresponding amine, containing at least one hydrogen atom, to obtain the desired group R.

An esterified carboxyl group R can, in a conventional manner, be converted to a free carboxyl group R, for example by hydrolysis in the presence of a catalyst, for example a basic or acid agent, such as a strong base, for example sodium hydroxide or potassium hydroxide, or a mineral acid, for example hydrochloric acid, sulfuric acid or phosphoric acid, or to an amidated carboxyl group R, for example by reaction with ammonia or the corresponding amine containing at least one hydrogen atom.

An esterified carboxyl group R can also be transesterified to another esterified carboxyl group R in a conventional manner, for example by reaction with a metal salt, such as the sodium or potassium salt, of a corresponding alcohol or with the alcohol itself in the presence of a catalyst, for example a strong base, for example sodium hydroxide or potassium hydroxide, or a strong acid, such as a mineral acid, for example hydrochloric acid, sulfuric acid or phosphoric acid, or an organic sulfonic acid, for example p-toluenesulfonic acid, or a Lewis acid, for example boron trifluoride etherate.

An amidated carboxyl group R can be converted to the free carboxyl group R in a conventional manner, for example by hydrolysis in the presence of a catalyst, for example a strong base, such as an alkali metal hydroxide or carbonate or alkaline earth metal hydroxide or carbonate, for example sodium hydroxide or carbonate or potassium hydroxide or carbonate, or a strong acid, such as a mineral acid, for example hydrochloric acid, sulfuric acid or phosphoric acid.

Furthermore, in a compound obtainable according to the invention free, esterified or etherified hydroxyl groups $R_2$ can be converted into one another.

Thus, for example, a free hydroxyl group $R_2$ can be esterified by reaction with a preferably functionally modified carboxylic acid, such as a lower alkanecarboxylic acid, for example acetic acid, to a hydroxyl group $R_1$ and/or $R_2$ esterified with a carboxylic acid or can be etherified by reaction with an etherifying agent, for example with a lower alkylating agent, to an etherified hydroxyl group, for example a lower alkoxy group, $R_1$ and/or $R_2$.

A functionally modified carboxylic acid is, for example, an anhydride, such as the symmetrical anhydride thereof, or an anhydride with a hydrogen halide acid, such as hydrochloric acid or hydrobromic acid, a reactive ester, i.e. an ester with electron-attracting structures, for example a phenyl, p-nitrophenyl or cyanomethyl ester of a lower alkanecarboxylic acid, or a reactive amide, for example a N-lower alkanoylimidazole or -3,5-dimethylpyrazole.

Etherifying agents are, for example, reactive esterified alcohols, such as alcohols esterified with a mineral acid, for example with hydriodic acid, hydrochloric acid or hydrobromic acid or sulfuric acid, or an organic sulfonic acid, for example with p-toluenesulfonic acid, p-bromobenzenesulfonic acid, benzenesulfonic acid, methanesulfonic acid, ethanesulfonic acid or ethenesulfonic acid, or fluorosulfonic acid, and also diazoalkanes. Suitable etherifying agents are in particular lower alkyl chlorides, lower alkyl iodides and lower alkyl bromides, for example methyl iodide, di-lower alkyl sulfates, for example dimethyl sulfate or diethyl sulfate, or methyl fluorosulfonate, lower alkyl sulfonates, such as lower alkyl, for example methyl, p-toluene-, p-bromobenzene-, methane- or ethane-sulfonates, and also diazoalkanes, for example diazomethane.

The reactions with acids, preferably functionally modified acids, and with etherifying agents, for example those singled out above, can be carried out in a conventional manner, and in the case of the reaction with a diazoalkane can be carried out, for example, in an inert solvent, such as an ether, for example in tetrahydrofuran, or when reactive esterified alcohols are used can be carried out, for example, in the presence of a basic condensing agent, such as an inorganic base, for example sodium hydroxide or carbonate, potassium hydroxide or carbonate or calcium hydroxide or carbonate, or a tertiary or quaternary nitrogen base, for example pyridine, α-picoline, quinoline, triethylamine or tetraethyl- or benzyltriethyl-ammonium hydroxide, and/or in the presence of a solvent which is customary for the particular reaction and which can also consist of an excess of the functional acid derivative used for the esterification, for example of a lower alkanoic acid anhydride or lower alkanoic acid chloride, or of the lower alkyl halide or lower alkyl sulfate used, for example, for the etherification, and/or of a tertiary nitrogen base used as a basic condensing agent, for example triethylamine or pyridine, if necessary at elevated temperature. It is advisable in particular to carry out methylation by means of methyl iodide in amyl alcohol/potassium carbonate at the boil and to carry out acylation by means of a lower alkanoic acid anhydride at 50°–150° or by means of a lower alkanoyl chloride in pyridine or pyridine/triethylamine at temperatures between −20° and +100° C.

Conversely, etherified or, in particular, esterified hydroxyl $R_2$ can also be converted to hydroxyl in a conventional manner, for example in the presence of an acid agent, such as a hydrogen halide acid, for example hydriodic acid, in an inert solvent, for example in ethanol or acetic acid.

Furthermore, in a compound obtainable according to the invention acyl $R_2$ and/or, in particular, $R_1$ can be replaced by hydrogen. Thus, a carboxyl group $R_2$ and/or, in particular, $R_1$ can be decarboxylated in a conventional manner, for example by the action of heat, or the acyl group $R_1$ of a carboxylic acid can be detached in a conventional manner, such as by the action of basic agents, such as alkalis, for example dilute sodium hydroxide solution or, in particular, sodium carbonate solution, preferably approximately 5% sodium carbonate solution.

Depending on the choice of the starting materials and procedures, the novel compounds can be in the form of one of the possible isomers or of a mixture thereof, for example in the form of isomers with respect to the orientation of X, and also, depending on the number of asymmetric carbon atoms, in the form of pure optical isomers, such as antipodes, or mixtures of isomers, such as racemates, mixtures of diastereomers or mixtures of racemates.

Resulting mixtures of isomers in respect of the orientation of X, mixtures of diastereomers and mixtures of racemates can be separated into the pure isomers, diastereomers or racemates in a known manner on the basis of the physico-chemical differences between the constituents, for example by chromatography and/or fractional crystallisation.

Resulting racemates can also be resolved into the optical antipodes by known methods, for example by recrystallisation from an optically active solvent, with the aid of micro-organisms, or by reacting an acid end product with an optically active base which forms salts with the racemic acid and separating the salts thus obtained, for example on the basis of their different solubilities, into the diastereomers, from which the antipodes can be liberated by the action of suitable agents. Advantageously, the more active of the two antipodes is isolated.

Resulting free compounds of the formula I, for example those in which R, $R_1$ and/or $R_2$ is carboxyl, can be converted to salts in a manner known per se, inter alia by treatment with a base or with a suitable salt of a carboxylic acid, usually in the presence of a solvent or diluent.

Resulting salts can be converted into the free compounds in a manner known per se, for example by treatment with an acid reagent, such as a mineral acid.

The compounds, including their salts, can also be obtained in the form of their hydrates or can incorporate the solvent used for crystallisation.

Because of the close relationship between the novel compounds in the free form and in the form of their salts, what is stated in this specification in respect of the free compounds or the salts thereof also applies by analogy to the corresponding salts and free compounds.

The invention also relates to those embodiments of the process in which a compound obtainable as an intermediate at any stage of the process is used as the starting material and the missing steps are carried out, or a starting material is used in the form of a salt and/or racemate or antipode or, in particular, is formed under the reaction conditions.

Thus, for example, in a modification of the cyclisation process according to the invention a compound of the formula

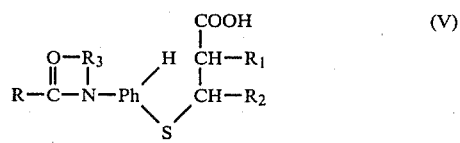

(V)

in which $R_1$, $R_3$, R and Ph are as defined and $R_2$ is hydrogen or a substituted or unsubstituted hydrocarbon radical, or a hetero-analogue thereof, can be used as the starting material and this can be reacted in the presence of an anhydride of phosphoric acid, for example with phosphorus pentoxide, phosphorus pentachloride or phosphorus oxychloride. A compound of the general formula (IV), for example a compound of this formula in which $Y_2$ is a group of the formula $-SCR_2=CR_1-COOH$ and $Y_1$ is hydrogen, is formed as an intermediate and is cyclised under the reaction conditions.

In an analogous manner, it is also possible to subject a compound of the formula

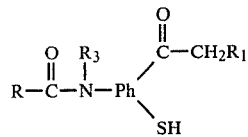
(VI)

to a condensation reaction with an acid of the formula $R_2-COOH$, which is in the form of an anhydride, for example in the form of a halide, such as the chloride, or in the form of a symmetrical anhydride, $R_1$ and $R_2$ in the formulae independently of one another being hydrogen or a substituted or unsubstituted hydrocarbon radical, or a hetero-analogue thereof, in the presence of a basic condensing agent, for example in the presence of an alkali metal carbonate, for example potassium carbonate in acetone, in the case of the reaction with an acid halide and, for example, in the presence of an alkali metal carboxylate or ammonium carboxylate, for example sodium acetate or the sodium salt of one of the acids corresponding to the anhydride used, in the case of the reaction with a symmetrical acid anhydride, to give a compound of the general formula (I) in which $-SX-$ is a group $-S-CR_2=CR_1-CO-$ and $R_1$ and $R_2$ are as defined above, or $R_1$ is a $R_2CO-$ group. A compound of the general formula IV in which $Y_1$ is a group $-COY_5$ of the formul $-COCH_2R_1$ and $Y_2$ is a group $-SOCY_6$ of the formula $-SOCR_2$ is formed as an intermediate and this is cyclised according to the invention, if necessary after prior acylation of the group $-COCH_2R_1$, for example of the formula $-COCH_3$, to a group $-CO-CHR_1-CO-R_2$, for example of the formula $-COCH_2COR_2$.

In another modification of the cyclisation process according to the invention, it is possible, for example, to subject a compound of the formula

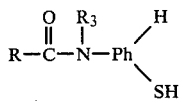
(VII)

in which R, $R_3$ and Ph are as defined initially, to a condensation reaction in the presence of a strongly acid condensing agent, such as a mineral acid, for example sulfuric acid, hydrochloric acid or hydrobromic acid, phosphoric acid or polyphosphoric acid, or of an aprotic acid condensing agent, such as an inorganic acid anhydride, for example phosphorus pentachloride or phosphorus oxychloride, with an ester of an acid of the formula $R_2-CO-CHR-COOH$, in which $R_1$ and $R_2$ independently of one another are hydrogen or a substituted or unsubstituted hydrocarbon radical, or a hetero-analogue thereof, to give compounds of the general formula (I) in which $-SX-$ is a group $-S-CR_2-CR_1-CO-$ in which $R_1$ and $R_2$ are as defined above. At least one compound of the general formula (IV), for example a compound of this formula in which $Y_1$ is a group of the formula $-COCHR_1-C(O)R_2-$ or a group of the formula $-CR_2(OH)-CHR_1-COOH$, the latter being in the form of an ester, and $Y_2$ is mercapto, and/or a compound of the said formula in which $Y_1$ is a group of the formula $-SCR_2=CR_1-COOH$, in the form of an ester, and $Y_2$ is hydrogen, is formed as an intermediate and this is cyclised according to the invention under the reaction conditions.

The starting materials are known or, if they are novel, can be prepared by methods known per se.

Thus, the starting materials of the general formula (II) can be prepared, for example, by, in a compound of the formula

(IIa)

in which Ph and X are as defined and R" is nitro or an acylated amino group which differs from the group of the formula $RCONR_3-$, converting the nitro group R" to primary amino by conventional reduction, for example catalytically or with a metal and an acid, for example with iron and hydrochloric acid, or sodium hyposulfite in aqueous ammonia, or converting an acylated amino group R" to an amino group $-NHR_3$ by conventional hydrolysis, preferably in the presence of an acid, such as a mineral acid, for example hydrochloric acid or sulfuric acid, or of an inorganic base, for example sodium hydroxide solution or potassium hydroxide solution. Primary amino first formed can easily be alkylated to $-NHR_3$, for example with a lower alkyl halide.

Starting materials of the general formula (II) can also be prepared by reacting a compound of the general formula

(IIb)

with an ester of an acid of the formula $R_2ClCHR_1COOH$, or, in a compound of the formula

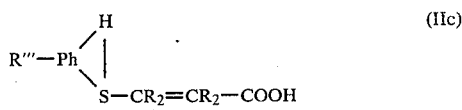
(IIc)

in which R''' is hydrogen or a group $-NHR_2$ or R", replacing hydrogen R''' by nitro by conventional nitration, reducing nitro to amino and, if necessary, hydrolysing acylamino to amino and/or alkylating amino to $-NHR_3$. The reaction is carried out in the conventional manner, for example in the presence of a strongly acid condensing agent, such as mineral acid, for example sulfuric acid, hydrochloric acid or hydrobromic acid, phosphoric acid or polyphosphoric acid, or preferably in the presence of an aprotic acid condensing agent, such as an acid anhydride, for example phosphorus pentoxide, phosphorus pentachloride or phosphorus oxychloride. The compounds of the formula IIa mentioned above as starting materials can also be prepared analogously.

Most of the compounds of the formula III mentioned as starting materials are novel. In addition to the fact that they can be used as starting materials for the preparation of compounds of the formula I, some of these compounds have further advantageous properties.

Thus, compounds of the formula III in which R' is a free or etherified glycoloylamino group have the same pharmacological properties, with comparable strength of action, as the corresponding compounds of the formula I.

The invention accordingly also relates to novel starting materials, in particular compounds of the formula III in which R' is a group of the formula $R_o$—$NHR_3$— and $R_o$ is a free or etherified glycoloyl group, processes for their preparation, pharmaceutical preparations containing these compounds and their use as pharmaceuticals or for the preparation of medicaments.

Etherified glycoloyl groups are, for example, glycoloyl groups etherified by a substituted or unsubstituted aliphatic or araliphatic alcohol, such as corresponding lower alkoxyacetyl or phenyl-lower alkoxyacetyl groups. Substituents of lower alkoxyacetyl are, in particular, hydroxyl, lower alkoxy and/or di-lower alkylamino and substituents of phenyl-lower alkoxyacetyl groups are, for example, lower alkyl, such as methyl, lower alkoxy, such as methoxy, and/or halogen, such as chlorine. Lower alkoxy preferably has one of the meanings defined initially and phenyl-lower alkoxyacetyl is in particular benzyloxyacetyl or 2-phenylethoxyacetyl. Di-lower alkylamino-lower alkoxyacetyl is preferably 2-dimethyl- or 2-diethyl-aminoethoxyacetyl.

The invention relates especially to those compounds of the formula III in which Ph and $R_1$ have the meanings defined for the particular preferred groups of compounds of the formula I, R' is a group $R_o$—$NHR_3$ and $R_o$ is lower alkoxyacetyl, in particular having not more than 6 carbon atoms, such as methoxyacetyl or ethoxyacetyl or preferably glycoloyl.

The compounds of the formula III mentioned as starting materials can be prepared by methods known per se, preferably by reacting a compound of the formula

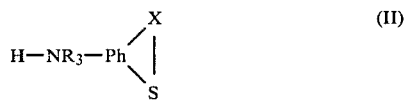   (II)

or an acid addition salt thereof, with a corresponding acid, for example of the formula $X_1$—OH (IIIa) or $X_2$—OH (IIIb), or a functional derivative thereof, and, if desired, converting a compound thus obtainable into another compound of the formula III in which R' is a group $R_o$—$NHR_3$.

Functional derivatives of acids of the formula IIIa and IIIb are, in particular, acid derivatives containing esterified or amidated carboxyl groups or carboxyl groups which have been converted to an anhydride, such as lower alkoxycarbonyl, substituted or unsubstituted carbamyl, for example carbamyl or imidazolyl-1-carbonyl, or halogenocarbonyl, for example chlorocarbonyl or bromocarbonyl, or a group of the formula —$CON_3$ or $CON_2^{\oplus}Hal^{\ominus}$. Examples of acids of the formula IIIa or IIIb and their functional derivatives are, in particular: as functional derivatives of acids of the formula IIIa, oxalyl halides, such as oxalyl chloride or oxalyl bromide, tri-lower alkoxy- and dihalogeno-lower alkoxyacetic acid lower alkyl esters, such as tetraethyl oxalate or diethyl dichloro-oxalate, oxalic acid iminodialkyl esters, such as mono- or di-iminodiethyl oxalate, oxalic acid amidines, such as N-lower alkyloxalic acid esteramidines, oxalic acid dithio-lower alkyl esters, such as dithiodimethyl oxalate, cyanoformyl chloride or cyanogen and, as acids of the formula IIIb and their functional derivatives, glycollic acid and its lower alkyl esters or the corresponding lactide, mono- or di-lower alkoxyacetic acid lower alkyl esters, such as mono- or di-lower alkoxyacetic acid ethyl esters, for example ethyl ethoxy acetate or ethyl diethoxy acetate, halogenoacetic anhydrides, such as chloroacetic anhydride and chloroacetyl chloride, and tartaric acid, or 2,3-diacetoxysuccinic anhydride, and also cinnamoyl chloride, acetyl chloride and glycine.

The reaction of compounds of the formula II with acids of the formula IIIa or IIIb and their derivatives can be carried out in a conventional manner, for example in the presence of a water-binding agent, such as an acid anhydride, for example phosphorus pentoxide, or dicyclohexylcarbodiimide, or of a condensing agent, for example an acid or basic condensing agent, such as a mineral acid, for example hydrochloric acid, or an alkali metal hydroxide or carbonate, for example sodium hydroxide or potassium hydroxide, or an organic nitrogen base, for example triethylamine or pyridine. In the case of the reaction with an acid anhydride, such as an acid chloride, the condensing agent used is preferably an organic nitrogen base. The reaction with carboxylic acids is preferably carried out in the presence of a water-binding agent. If necessary, the reaction is in each case carried out in an inert solvent, at normal temperature or with cooling or warming, for example in the temperature range from about 0° C. to about 100° C., in a closed vessel and/or under an inert gas, for example nitrogen.

Compounds of the formula III in which R's is a group R—CH=N— can be prepared analogously by a condensation reaction with free, esterified or amidated glyoxylic acid.

Compounds of the formula III in which R' is a —$NHR_3$—$X_2$ group and $X_2$ is glyoxyloyl can also be prepared by heating a corresponding halogeno-acetyl compound, such as a bromoacetyl compound, with hexamethylenetetramine, preferably in an aqueous alcohol or by oxidising the said halogenoacetyl compound with silver tetrafluoborate in dimethylsulfoxide. Analogously, it is also possible to oxidise a chloroacetyl compound with potassium dichromate in hexamethylphosphoric acid triamide in the presence of dicyclohexyl-18-crown-6 ether. Compounds of the formula III in which R' is a $X_2$—$NHR_3$— group and $X_2$ is an iminoacetyl group, for example substituted or unsubstituted benzyliminoacetyl, can be prepared using corresponding glycyl compounds as the starting materials, by reacting these compounds with the corresponding carbonyl compound, for example with benzaldehyde, and rearranging the intermediate thus obtainable, for example a benzylideneglycyl compound, preferably under the reaction conditions.

Functionally modified oxalo groups containing an imino-ether grouping as a functionally modified carboxyl group can be prepared using the corresponding cyanocarbonyl compound as the starting material, by reaction with the corresponding alcohol, for example lower alkanol or lower alkanediol or amino-lower alkanol.

The compounds, according to the invention, of the formula III in which R' is a group of the formula $R_o$—$NHR_3$— and $R_o$ is a free or etherified glycoloyl group can also be prepared by, in a compound of the formula III in which R' is a radical which can be converted to the group $R_oNHR_3$—, converting the radical R' to the desired group $R_o$—$NHR_3$— and, if desired, converting a compound thus obtainable into another compound of the formula III in which R' is a R$_o$NH-R$_3$— group.

Radicals which can be converted to a R$_o$—NHR$_3$— group are, for example, those of the formula X$_1$'—NH-R$_3$—, in which X$_1$' is an esterified glycoloyl group, for example a glycoloyl group esterified with a mineral acid, for example with a hydrogen halide acid, such as chloroacetyl or bromoacetyl. Such groups X$_1$' can be converted to the glycoloyl group by hydrolysis, for example in the presence of a basic hydrolysing agent, such as sodium hydroxide solution, or can be converted to etherified glycoloyl groups by reaction with a salt, such as an alkali metal salt, for example the sodium salt, of a corresponding alcohol.

Further radicals R' which can be converted to groups of the formula R$_o$—NHR$_3$— are those of the formula X$_2$'NHR$_3$—, in which X$_2$' is a radical which can be converted to the glycoloyl group by reduction, such as the glyoxyl group, which can be in the form of a hydrate. This group can also be formed under the reaction conditions, for example from the oxalo group, which can be in the form of a salt, such as in the form of the sodium salt, or in the form of an anhydride or ester, such as in the form of halogenooxalyl, for example chlorooxalyl or bromooxalyl, or of a mixed anhydride with diphenylphosphoric acid or in the form of a lower alkyl ester, for example in the form of the methyl or isopropyl ester. The reduction of such groups is carried out in the conventional manner. When the starting group is halogenooxalyl, catalytically activated hydrogen is preferably used, for example hydrogen catalytically activated by palladium on a support, such as barium sulfate, if necessary in the presence of a sulfur-containing co-catalyst, such as thiourea. Anhydrides with diphenylphosphoric acid are advantageously reduced with an excess of sodium borohydride. Oxalo groups in the form of a salt are advantageously reduced using a borene, such as diborane or a borane/ether complex, for example with borane in tetrahydrofuran, whilst oxalo groups in the form of an ester are advantageously reduced with sodium anilinoborohydride, which is obtainable by reaction of sodium borohydride and acetanilide in pyridine.

The compounds, according to the invention, of the formula III in which R' is a R$_o$—NHR$_3$— group can also be prepared by a process strictly analogous to the cyclisation processes described above which result in compounds of the formula I, by using a starting material of the formulae IV, V, VI or VII, in which the radical Ph carries the desired group R$_o$—NHR$_3$— in place of the group R—C(=O)—NR$_3$—. The starting materials for this reaction can also be prepared by procedures analogous to those described below for the starting materials to be used for the preparation of compounds of the formula I.

A compound, according to the invention, of the formula III which is thus obtainable can be converted to another compound, according to the invention, of the formula III.

Thus, for example, the conversions of free, esterified or etherified hydroxyl groups R$_2$ into one another and the separation of isomers in respect of the orientation of X can be applied to the compounds according to the invention.

Furthermore, glycoloyl groups R$_o$ can be etherified by reaction with an etherifying agent, for example by conversion to an alkali metal salt, such as the sodium salt, and reaction with a reactive derivative of the particular alcohol, such as a lower alkyl halide, for example lower alkyl bromide, or di-lower alkyl sulfate.

The starting materials of the general formula IV can be prepared, for example, by, in a compound of the formula

in which R" is acylamino other than RCONR$_3$—, nitro or amino and R, Ph, Y$_1$ and Y$_2$ are as defined, converting acylamino R" to —NHR$_3$ by conventional hydrolysis or converting nitro R" to amino by conventional nitro reduction, lower alkylating if necessary and acylating —NHR$_3$ in the conventional manner to the desired group of the formula RCO—, for example by reaction with a compound of the formula R—CO—Hal, in which R is as defined and Hal is chlorine or bromine, preferably in the presence of a basic condensing agent, such as a tertiary organic nitrogen base, for example pyridine or triethylamine. Nitro compounds (IV') are reduced, for example, with sodium dithionite or with iron and hydrochloric acid or with zinc and acetic acid. Corresponding acylamino compounds containing an acylamino radical which differs from the group of the formula RCONR$_3$ are hydrolysed, for example, in the presence of an acid or basic agent, for example hydrochloric or sulfuric acid or sodium hydroxide solution or potassium hydroxide solution.

Starting materials of the formula (IV) in which Y$_1$ is a group —CO—CR$_1$=CR$_2$Y$_4$ of the formula —COCH-R$_1$—C(O)R$_2$—, in which R$_2$ is hydrogen or a substituted or unsubstituted hydrocarbon radical, or a hetero-analogue thereof, and Y$_2$ is free or etherified mercapto, can also be prepared by subjecting compounds of the formulae

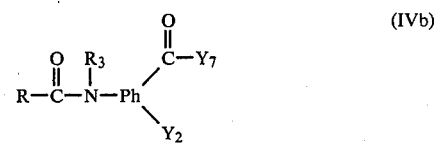

and R$_2$CO—Y$_8$ (IVc) in which one of the radicals Y$_7$ and Y$_8$ is a group —CH$_2$R$_1$ and the other is etherified mercapto, such as lower alkylthio, for example methylthio or ethylthio, and R, R$_1$, R$_3$ and Ph are as defined initially and Y$_2$ and R$_2$ are as defined above, to a conventional ester condensation, for example to reaction in the presence of a strongly basic condensing agent, such as an alkali metal or the hydride thereof or an amide or alcoholate of an alkali metal, for example sodium, sodium hydride, diisopropylamine-lithium or sodium methylate, and, if desired, subjecting a group of the formula —COCH$_2$-C(O)R$_2$— formed from a starting compound in which R$_1$ is hydrogen to α-substitution in the conventional manner, for example by conversion to an α-metal salt, preferably by reaction with one of the said strongly basic condensing agents, for example with diisopropylamine-lithium, and subsequent reaction with a halide, for example chloride or bromide, of the desired substituted or unsubstituted hydrocarbon, or hetero-analogue thereof, or of the acid corresponding to the desired acyl radical R₁.

Starting materials of the general formula (IV) in which Y₁ is a group of the formula —SCR₂=CR₁—COOH, which can be in the form of an ester, and R₂ is hydrogen or a substituted or unsubstituted hydrocarbon radical, or a hetero-analogue thereof, and Y₂ is hydrogen can also be prepared by subjecting a compound of the formula IVd and a compound of the formula IVe

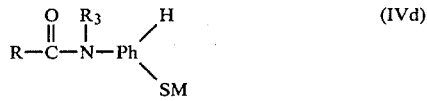

and Y₉—CR₂=Y₁₀—COOH (IVe)
in which formulae either Y₉ is halogen, for example chlorine or bromine, and Y₁₀ is a radical R₁, or Y₉ and Y₁₀ together are an additional bond, R₁, R, R₃ and Ph are as defined initially and R₂ is as defined above and M is an alkali metal, for example sodium, to a condensation reaction in the conventional manner, the compound of the formula IVe being in the form of an ester, for example in the form of the methyl or ethyl ester.

Starting materials of the general formula (IV) in which Y₂ is free or etherified mercapto or mercapto esterified with a carboxylic acid and Y₁ is a group of the formula —CR₂=CR₁—Y₃, in which R₂ is hydrogen or a substituted or unsubstituted hydrocarbon radical, or a hetero-analogue thereof, can also be prepared by subjecting a compound of the formula IVf and a compound of the formula IVg, which is preferably in the form of an ester,

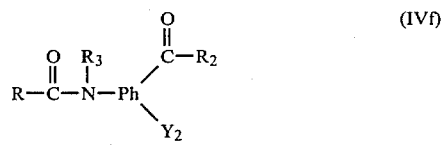

and Y₁₁—CHR₁—Y₃ (IVg)
in which formulae R₁, R, R₃ and Ph are as defined initially and R₂ is as defined above and Y₁₁ is hydrogen or halogen, for example bromine or chlorine, to a condensation reaction in the conventional manner, preferably in the presence of zinc in the case of the reaction with α-halogeno esters or by means of potassium carbonate and acetone in the case of the reaction with esters, and, in the resulting condensation product, if desired converting etherified hydroxyl Y₂ to hydroxyl in the conventional manner, for example by means of hydriodic acid.

The synthesis reactions which result in starting materials of the general formula (IV), for example the reactions described above, can, however, also be carried out in a different order. Thus, for example, in place of the said starting compounds IVb, IVd or IVf, compounds of the formulae IVh, IVi or IVj

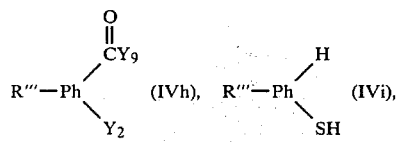

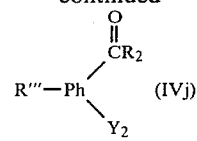

in which R‴ is hydrogen, nitro, a —NHR₃ group or acylated amino other than the group RCONR₃—, can be subjected to a condensation reaction in the indicated manner and, in the resulting compound of the formula (IIIa), the group R‴ can be converted to the desired group RCO— in the indicated manner.

The starting materials used in the process of the present invention are preferably those which result in the compounds described initially as being particularly valuable.

The present invention also relates to pharmaceutical preparations which contain one of the compounds, according to the invention, of the formula I or III or a pharmaceutically acceptable salt thereof. The pharmaceutical preparations according to the invention are those intended for topical and local application and for enteral, such as oral or rectal, and parenteral administration to and for inhalation by warm-blooded animals and contain the pharmacological active ingredient on its own or together with a pharmaceutically acceptable carrier. The dosage of the active ingredient depends on the species of warm-blooded animal, the age and the individual condition, and also on the mode of administration.

The novel pharmaceutical preparations contain, for example, from about 10% to about 95% and preferably from about 20% to about 90% of the active ingredient. Pharmaceutical preparations according to the invention are, for example, those in aerosol or spray form or in the form of dosage units, such as sugar-coated tablets, tablets, capsules or suppositories, and also ampoules.

The pharmaceutical preparations of the present invention are prepared in a manner known per se, for example by conventional mixing, granulating, sugar-coating, dissolving or lyophilising methods. Thus, pharmaceutical preparations for oral use can be obtained by combining the active ingredient with solid carriers, if desired granulating a mixture thus obtained and processing the mixture or granules, if desired or necessary after the addition of suitable adjuncts, to tablets or sugar-coated tablet cores.

Suitable carriers are in particular fillers, such as sugars, for example lactose, sucrose, mannitol or sorbitol, cellulose preparations and/or calcium phosphates, for example tricalcium phosphate or calcium hydrogen phosphate, and also binders, such as starch pastes, for example maize, corn, rice or potato starch paste, gelatin, tragacanth, methylcellulose and/or polyvinylpyrrolidone, and/or, if desired, disintegrators, such as the above starches and also carboxymethyl-starch, cross-linked polyvinylpyrrolidone, agar, alginic acid or a salt thereof, such as sodium alginate. Adjuncts are in particular glidants and lubricants, for example silica, talc, stearic acid or salts thereof, such as magnesium stearate or calcium stearate, and/or polyethylene glycol. Sugar-coated tablet cores are provided with suitable coatings which can be resistant to gastric juices, using, inter alia, concentrated sugar solutions which may contain gum arabic, talc, polyvinylpyrrolidone, polyethylene glycol and/or titanium dioxide, shellack solutions in suitable organic solvents or solvent mixtures or, for the preparation of coatings resistant to gastric juices, solutions of suitable cellulose preparations, such as acetylcellulose phthalate or hydroxypropylmethylcellulose phthalate. Dyes or pigments can be added to the tablets or the coatings of sugar-coated tablets, for example to identify or indicate different doses of active ingredient.

Further pharmaceutical preparations for oral administration are dry-filled capsules made of gelatin and also soft, sealed capsules made of gelatin and a plasticiser, such as glycerol or sorbitol. The dry-filled capsules can contain the active ingredient in the form of granules, for example mixed with fillers, such as lactose, binders, such as starches, and/or lubricants, such as talc or magnesium stearate, and, if desired, stabilisers. In soft capsules, the active ingredient is preferably dissolved or suspended in suitable liquids, such as fatty oils, paraffin oil or liquid polyethylene glycols, to which stabilisers can also be added.

Pharmaceutical preparations for rectal administration are, for example, suppositories, which consist of a combination of the active ingredient with a suppository base. Examples of suitable suppository bases are natural or synthetic triglycerides, paraffin hydrocarbons, polyethylene glycols or higher alkanols. Gelatin rectal capsules which contain a combination of the active ingredient with a base can also be used; suitable base materials are, for example, liquid triglycerides, polyethylene glycols or paraffin hydrocarbons.

Preparations suitable for parenteral administration are in particular aqueous solutions of an active ingredient in a water-soluble form, for example of a water-soluble salt, and also suspensions of the active ingredient, such as corresponding oily injection suspensions, for which suitable lipophilic solvents or vehicles, such as fatty oils, for example sesame oil, or synthetic fatty acid esters, for example ethyl oleate or triglycerides, are used, or aqueous injection suspensions which contain substances which increase the viscosity, for example sodium carboxymethylcellulose, sorbitol and/or dextran and, if desired, also stabilisers.

Inhalation preparations for the treatment of the respiratory passages by nasal or buccal administration are, for example, aerosols or sprays, which can disperse the pharmacological active ingredient in the form of a powder or in the form of drops of a solution or suspension. Preparations with powder-dispersing properties usually contain, in addition to the active ingredient, a liquid propellant gas with a boiling point below room temperature and also, if desired, carriers, such as liquid or solid non-ionic or anionic surface-active agents and/or diluents. Preparations in which the pharmacological active ingredient is in solution contain, in addition to this ingredient, a suitable propellant and also, if necessary, an additional solvent and/or a stabiliser. In place of the propellant gas it is also possible to use compressed air, and this can be produced as required by means of a suitable compression and pressure-release device.

Pharmaceutical preparations for topical and local use are, for example, lotions and creams, which contain a liquid or semi-solid oil-in-water or water-in-oil emulsion, and ointments (which preferably contain a preservative), for the treatment of the skin, eyedrops, which contain the active compound in aqueous or oily solution, and eye ointments, which are preferably prepared in sterile form, for the treatment of the eyes, and, for the treatment of the nose, powders, aerosols and sprays (similar to those described above for the treatment of the respiratory passages), and also coarse powders, which are administered by rapid inhalation through the nostrils, and nose-drops, which contain the active compound in aqueous or oily solution, or, for local treatment of the mouth, lozenges, which contain the active compound in a composition which is generally formed from sugar and gum arabic or tragacanth and to which flavourings can be added, and also pastilles, which contain the active ingredient in an inert composition, for example of gelatin and glycerol or sugar and gum arabic.

The invention also relates to the use of the novel compounds of the formula (I) and their salts as pharmacologically active compounds and especially as anti-allergic agents, preferably in the form of pharmaceutical preparations. The daily dose which is administered to a warm-blooded animal weighing about 70 kg is from about 200 mg to about 1,200 mg.

The following examples illustrate the present invention without in any way restricting the scope thereof. Temperatures are given in degrees centigrade.

EXAMPLE 1

A solution of 6.8 g of oxalic acid monomethyl ester-chloride in 20 ml of dimethylformamide is added dropwise to a solution of 8.4 g of 2-methyl-7-amino-4-oxo-4H-1-benzothiopyran in 80 ml of dimethylformamide and 5.6 g of triethylamine, with stirring. The rate of the dropwise addition is so regulated that the internal temperature does not rise above 35°. The reaction mixture is stirred for a further 2 hours at room temperature and poured into 1,200 ml of ice-water and the precipitate which has separated out is filtered off with suction. This precipitate is dried and twice recrystallised from a mixture of, in each case, 200 ml of chloroform and 100 ml of methanol. 2-Methyl-7-methoxyoxalylamino-4-oxo-4H-1-benzothiopyran with a melting point of 224° (decomposition) is obtained.

The starting material can be prepared as follows:

12 ml of ethyl chloroformate are added dropwise to a solution of 25 g of 3-aminothiophenol in 150 ml of ethyl acetate at 50°, under gentle reflux. 50 ml of ethyl acetate are added and the reaction mixture is boiled under reflux for 5 minutes, cooled to 40° and filtered with suction. The filtrate is evaporated to dryness and the oily evaporation residue is chromatographed on silica gel using toluene as the solvent. 3-Ethoxycarbonylamino-thiophenol is obtained by evaporating the eluate. 10 g of this product are mixed with 8 g of ethyl acetoacetate and the mixture is added dropwise to 153 g of polyphosphoric acid at 90°. The mixture is warmed for 2 hours at an internal temperature of 95° and the hot reaction mixture is poured into 2 liters of ice-water, the resulting mixture is stirred for 30 minutes and the precipitate which has separated out is filtered off with suction. 2-Methyl-7-ethoxycarbonylamino-4-oxo-4H-1-benzothiopyran is thus obtained and after recrystallisation from 70 ml of ethanol this melts at 216°–218°. 15.6 g of this product are refluxed with 28.7 ml of sulfuric acid and 52 ml of acetic acid for 5 hours. The reaction mixture is poured into 500 ml of ice-water and the resulting mixture is neutralised with sodium hydroxide solution. 2-Methyl-7-amino-4-oxo-4H-1-benzothiopyran with a melting point of 165°–169° is obtained and this can be purified via the hydrochloride and then melts at 172°–175°.

EXAMPLE 2

6.6 g of 2-methyl-7-methoxyoxalylamino-4-oxo-4H-1-benzothiopyran are suspended in 240 ml of 0.1 N sodium hydroxide solution. The suspension is stirred for 2 hours at 40° and filtered, the filtrate is acidified with 2 N hydrochloric acid and the crude product which has separated out is collected and boiled thoroughly, first with dimethylformamide and then with ethanol. 2-Methyl-7-oxaloamino-4-oxo-4H-1-benzothiopyran with a melting point of 250° (decomposition) is obtained.

EXAMPLE 3

A solution of 10.7 g of oxalic acid monomethyl ester-chloride in 24 ml of dimethylformamide is added dropwise to a solution of 13.3 g of 2-methyl-6-amino-4-oxo-4H-1-benzothiopyran in 8.9 g of triethylamine and 360 ml of dimethylformamide. The reaction mixture is stirred for 2 hours and poured into 1,200 ml of ice-water and the precipitate which has separated out is filtered off with suction, dried and recrystallised from dimethylformamide/methanol. 2-Methyl-6-methoxyoxalylamino-4-oxo-4H-1-benzothiopyran with a melting point of 260°–262° is obtained.

The starting material can be prepared in a manner analogous to that described in Example 1, preferably by reacting 50 g of 4-aminothiophenol in 300 ml of ethyl acetate with 24 ml of ethyl chloroformate to give the corresponding ethoxycarbonyl compound with a melting point of 60°–61° (from ether/hexane, 70 ml), reacting this compound with 8 g of ethyl acetoacetate and 153 g of polyphosphoric acid to give 2-methyl-6-ethoxycarbonylamino-4-oxo-4H-1-benzothiopyran with a melting point of 219°–220° (from ethanol) and reacting the latter with 12.7 ml of sulfuric acid and 23 ml of acetic acid to give 2-methyl-6-amino-4-oxo-4H-1-benzothiopyran with a melting point of 265° (from ethanol).

EXAMPLE 4

2-Methyl-6-oxaloamino-4-oxo-4H-1-benzothiopyran with a melting point of 238°–240° (from dimethylformamide) is obtained in a manner analogous to that described in Example 2, by reacting 13 g of 2-methyl-6-methoxyoxalylamino-4-oxo-4H-1-benzothiopyran with 470 ml of 0.1 N sodium hydroxide solution.

EXAMPLE 5

The following compounds can also be prepared in a manner analogous to that described in Examples 1–4: 2,3-dimethyl-7-methoxyoxalylamino-4-oxo-4H-1-benzothiopyran, 2,3-dimethyl-7-oxaloamino-4-oxo-4H-1-benzothiopyran, 2-phenyl-7-methoxyoxalylamino-4-oxo-4H-1-benzothiopyran and 2-phenyl-6-oxaloamino-4-oxo-4H-1-benzothiopyran.

EXAMPLE 6

Tablets containing 0.1 g of 2-methyl-7-oxaloamino-4-oxo-4H-1-benzothiopyran are prepared as follows:

| Composition (for 1,000 tablets): | |
| --- | --- |
| 2-methyl-7-oxaloamino-4-oxo-4H-1-benzothiopyran | 100 g |
| lactose | 50 g |
| corn starch | 73 g |
| colloidal silica | 13 g |
| magnesium stearate | 2 g |
| talc | 12 g |
| water | q.s. |

The 2-methyl-7-oxaloamino-4-oxo-4H-1-benzothiopyran is mixed with a portion of the corn starch and with the lactose and the colloidal silica and the mixture is forced through a sieve. A further portion of the corn starch is mixed to a paste with five times the amount of water on a waterbath and the above powder mixture is kneaded with this paste until a slightly plastic mass has formed. The plastic mass is pressed through a sieve of about 3 mm mesh width and dried and the dry granules are again forced through a sieve. The remainder of the corn starch, the talc and the magnesium stearate are then mixed in and the resulting mixture is compressed to tablets weighing 0.25 g (with a breaking notch).

Tablets in each case containing 100 mg of one of the compounds of the general formula I named in Examples 1 and 2 can also be prepared in an analogous manner.

EXAMPLE 7

An approximately 2% aqueous solution, suitable for inhalation, of an active substance according to the invention, which is water-soluble in the free form or in the form of the sodium salt, can be prepared, for example, in the following composition:

| Composition: | |
| --- | --- |
| active ingredient, for example 2-methyl-7-oxaloamino-4-oxo-4H-1-benzothiopyran | 2,000 mg |
| stabiliser, for example disodium ethylenediaminetetraacetate | 10 mg |
| preservative, for example benzalkonium chloride | 10 mg |
| freshly distilled water | to make up to 100 mg |

Preparation

The active ingredient is dissolved in freshly distilled water with the addition of the equimolecular amount of 2 N sodium hydroxide solution. The stabiliser and the preservative are then added. After all of the components have dissolved completely, the resulting solution is made up to 100 ml and filled into small bottles and these are sealed gas-tight.

2% inhalation solutions containing a target compound of one of Examples 1, 2 and 4 as the active ingredient can also be prepared in an analogous manner.

EXAMPLE 8

Capsules which are suitable for insufflation and contain about 25 mg of an active substance according to the invention can be prepared, for example, in the following composition:

| Composition | |
| --- | --- |
| active ingredient, for example 2-methyl-7-methoxyoxalylamino-4-oxo-4H-1-benzothiopyran | 25 g |
| lactose, very finely ground | 25 g |

Preparation

The active ingredient and the lactose are intimately mixed and the resulting powder is then sieved and filled in 50 mg portions into 1,000 gelatin capsules.

Insufflation capsules each containing a target compound according to one of Examples 2 to 5 can also be prepared in an analogous manner.

What is claimed is:

1. A benzothiopyran derivative of the general formula

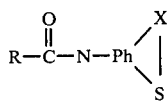  (I)

in which R is carboxy or lower alkoxycarbonyl, Ph is 1,2-phenylene containing the group R—CO—NR$_3$— or said 1,2-phenylene group substituted by lower alkyl, lowr alkoxy, halogen or trifluoromethyl, X is a group of the formula —CO—CR$_1$=CR$_2$—, in which R$_1$ and R$_2$ independently of one another are hydrogen, lowr alkanoyl, lower alkyl or phenyl or together are 3-membered to 5-membered lower alkylene and R$_2$ can also be hydroxy, lower alkoxy or lowr alkanoyloxy, and R$_3$ is hydrogen or lowr alkyl or a pharmaceutically acceptable salt thereof.

2. A compound according to claim 1 in which R is carboxy or lower alkoxycarbonyl, Ph is 1,2-phenylene containing the group R—CO—NR$_3$ or said 1,2-phenylene group substituted by lower alkyl, lower alkoxy, halogen or trifluoromethyl X is a group of the formula —CO—CR$_1$=CR$_2$—, in which R$_1$ and R$_2$ independently of one another are hydrogen, lower alkanoyl, lower alkyl or phenyl or together are 1,3-,1,4- or 1,5- lower alkylene and R$_2$ can also be hydroxy, lower alkoxy or lower alkanoyloxy, and R$_3$ is hydrogen or lower alkyl or a pharmaceutically acceptable salt thereof.

3. A compound according to claim 1, of the general formula Ia

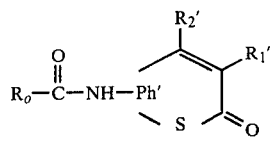  (Ia)

or of the general formula Ib

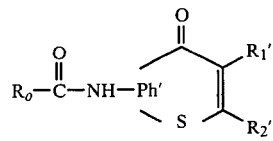  (Ib)

in which R$_0$ is carboxy or lower alkoxycarbonyl, Ph is 1,2-phenylene containing the group R—CO—NR$_3$— or said 1,2-phenylene group substituted by lower alkyl, lower alkoxy, halogen or trifluoromethyl, and R$_1$' and R$_2$' together are tri-, tetra- or penta-methylene, or R$_1$' is hydrogen, lowr alkanoyl, lower alkyl or phenyl and R$_2$ has one of the meanings defined for R$_1$' or is hydroxy, lowr alkoxy or lower alkanoyloxy or a pharmaceutically acceptable salt thereof.

4. A compound according to claim 1, of the formula

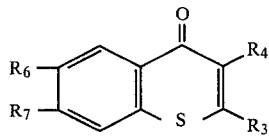  (Ic)

in which one of the radicals R$_6$ and R$_7$ is a group of the formula R$_0$'—CO—NH, in which R$_0$' is carboxyl or lower alkoxycarbonyl having not more than 5 C atoms, and the other is hydrogen, and R$_3$ and R$_4$ independently of one another are hydrogen or lower alkyl having not more than 4 C atoms, in the free form or in the form of a salt.

5. A compound as claimed in claim 1 being 2-Methyl-7-methoxyoxalylamino-4-oxo-4H-1-benzothiopyran.

6. A compound as claimed in claim 1 being 2-Methyl-7-oxaloamino-4-oxo-4H-1-benzothiopyran or a salt thereof.

7. A compound as claimed in claim 1 being 2-Methyl-6-methoxyoxalylamino-4-oxo-4H-1-benzothiopyran.

8. A compound as claimed in claim 1 being 2-Methyl-6-oxaloamino-4-oxo-4H-1-benzothiopyran or a salt thereof.

9. A compound as claimed in claim 1 being 2,3-Dimethyl-7-methoxyoxalylamino-4-oxo-4H-1-benzothiopyran,
2,3-Dimethyl-7-oxaloamino-4-oxo-4H-1-benzothiopyran or a salt thereof,
2-Phenyl-7-methoxyoxalylamino-4-oxo-4H-1-benzothiopyran or
2-Phenyl-6-oxaloamino-4-oxo-4H-1-benzothiopyran or a salt thereof.

10. A pharmaceutical preparation comprising an antiphlogistically effective amount of a compound of claim 1 together with a pharmaceutically acceptable carrier.

* * * * *